United States Patent [19]
Bargain et al.

[11] 4,208,342
[45] Jun. 17, 1980

[54] POLYETHYLENE SILICON COMPOUNDS

[75] Inventors: Michel Bargain, Lyons; Marcel Lefort, Caluire, both of France

[73] Assignee: Rhone-Poulenc Industries, Paris, France

[21] Appl. No.: 817,341

[22] Filed: Jul. 20, 1977

[30] Foreign Application Priority Data

Aug. 17, 1976 [FR] France ................................ 76 25535

[51] Int. Cl.² ............................ C07F 7/08; C07F 7/10
[52] U.S. Cl. ..................................... 556/436; 546/14; 556/441; 260/347.3; 260/347.4; 549/4; 260/326.47; 260/326.2
[58] Field of Search ................................ 260/448.2 Q

[56] References Cited

U.S. PATENT DOCUMENTS

4,088,670   5/1978   Bargain et al. ............... 260/448.2 Q

*Primary Examiner*—Paul F. Shaver
*Attorney, Agent, or Firm*—Burns, Doane, Swecker & Mathis

[57] ABSTRACT

Novel organosilicon compounds and processes for their preparation are disclosed. The compounds are di- and trisilanes of the formula

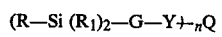

$(R-Si(R_1)_2-G-Y)_n Q$ in which R represents a radical containing one double ethylene bond, $R_1$ represents a hydrocarbon radical, G represents a carbocyclic aromatic or heterocyclic radical, Y represents CONH or COO, Q represents an organic radical and n is an integer equal to 2 or 3. The compounds are useful in preparing thermoplastic elastomers.

7 Claims, No Drawings

POLYETHYLENE SILICON COMPOUNDS

BACKGROUND OF THE INVENTION

1. Field of the Invention:

The present invention is directed to novel organosilicon compounds containing functional groups including an ethylene double bond, and methods of preparing them.

2. Description of the Prior Art:

The use of organosilicon compounds in preparing thermoplastic elastomers is well recognized in the art. For example, in Belgian Pat. No. 834,046, published Mar. 30, 1976, polysiloxane thermoplastic elastomers are formed from recurrent groups of silicon bonded to oxygen upon which other functional groups may be attached to form complex, branched chain thermoplastic polymers.

SUMMARY OF THE INVENTION

It is a primary object of the invention to provide novel organosilicon compounds containing functional groups which include carbon-carbon double bonds. Such compounds are useful in the production of thermoplastic elastomers.

Another object of the invention is to provide a process for the preparation of the novel organosilicon compounds.

Other objects and advantages of the present invention will become evident to those of skill in the art after reading the detailed description which follows.

DETAILED DESCRIPTION OF THE INVENTION

The compounds of the present invention are organosilicon compounds of the formula:

$$(R-Si(R_1)_2-G-Y)_n Q \qquad (I)$$

in which:

The symbol n is equal to 2 or 3;

The symbol R represents a monovalent hydrocarbon radical containing as many as 10 atoms of carbon and including a carbon-carbon double bond;

The symbol $R_1$ represents a monovalent hydrocarbon radical, which has been selected from among linear or branched alkyl radicals with at the most 10 carbon atoms—radicals which can be replaced by one or several halogen atoms or cyano groups; cycloalkyl radicals with 3 to 6 carbon atoms in the cycle; aryl radicals. The cycloalkyl or aryl radicals can be replaced by one or several halogen atoms;

The symbol G represents an aromatic carbocyclic radical or a heterocyclic radical. These radicals can be mono- or polycyclic, when polycyclic can be condensed or combined by a simple bond or by an atom or group such as —O—, —CH$_2$—, —C(CH$_3$)$_2$—, —C(CH$_3$)$_2$—, —SO$_2$—, —CONH—;

The symbol Q represents a radical of n valence, selected from the group consisting of aliphatic radicals with up to 13 carbon atoms, cycloaliphatic radicals with 5 or 6 carbon atoms in the cycle, heterocyclic radicals, aromatic radicals containing one or several benzene nuclei. When there are several benzene nuclei they can be condensed or related by a simple bond or by an atom or group such as —CH$_2$—, —C(CH$_3$)$_2$, —O—,

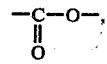

—CONH—;

The symbol Y represents a group selected from the group consisting of —CONH— and —COO—. The radicals represented by the symbols R, $R_1$, G, and Y may be different from one motif [R—Si($R_1$)$_2$—G—Y] to another.

According to a preferred embodiment of the present invention, the symbols referred to above are given the following meaning:

n is an integer equal to 2 or 3;

R represents a radical selected from the group consisting of vinyl, allyl, dichloro-2, 2 vinyl, trichloro-1,2,2 vinyl, butene-2 yl, propene-1 yl, butene-1 yl, methyl-2 propene-1 yl;

$R_1$ represents a radical selected from the group consisting of methyl, ethyl, trifluoro-4,4,4 butyl, phenyl, o-, m- or p-tolyl, xylyl, p- or m-chlorophenyl, dichloro-3,5 phenyl, trichlorophenyl, tetrachlorophenyl, β-cyanoethyl and γ-cyanopropyl;

G represents a radical selected from the group consisting of:

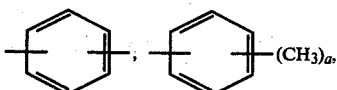

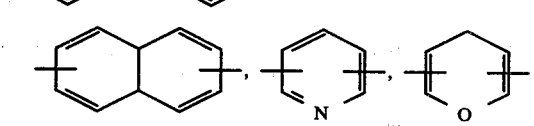

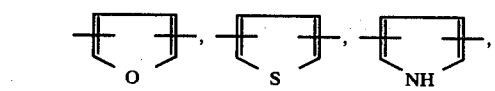

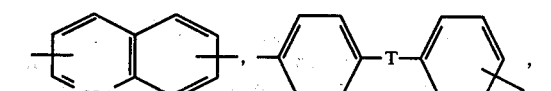

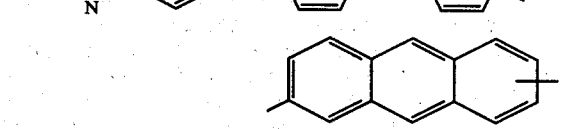

wherein a is equal to 1 or 2 and T represents a simple bond or O, CH$_2$, C(CH$_3$)$_2$ or SO$_2$;

Q represents a divalent radical selected from the group consisting of pentamethylene, hexamethylene, cyclohexylene, one of the radicals illustrated above in defining G and radicals containing up to 5 benzene nuclei related to each other by simple bonds or one of the following groups: O, CH$_2$, C(CH$_3$)$_2$, SO$_2$, COO, or CONH.

Alternatively, Q may be a trivalent radical corresponding to the divalent radicals listed above.

The following formulas represent organosilicon compounds which are within the scope of the present invention:

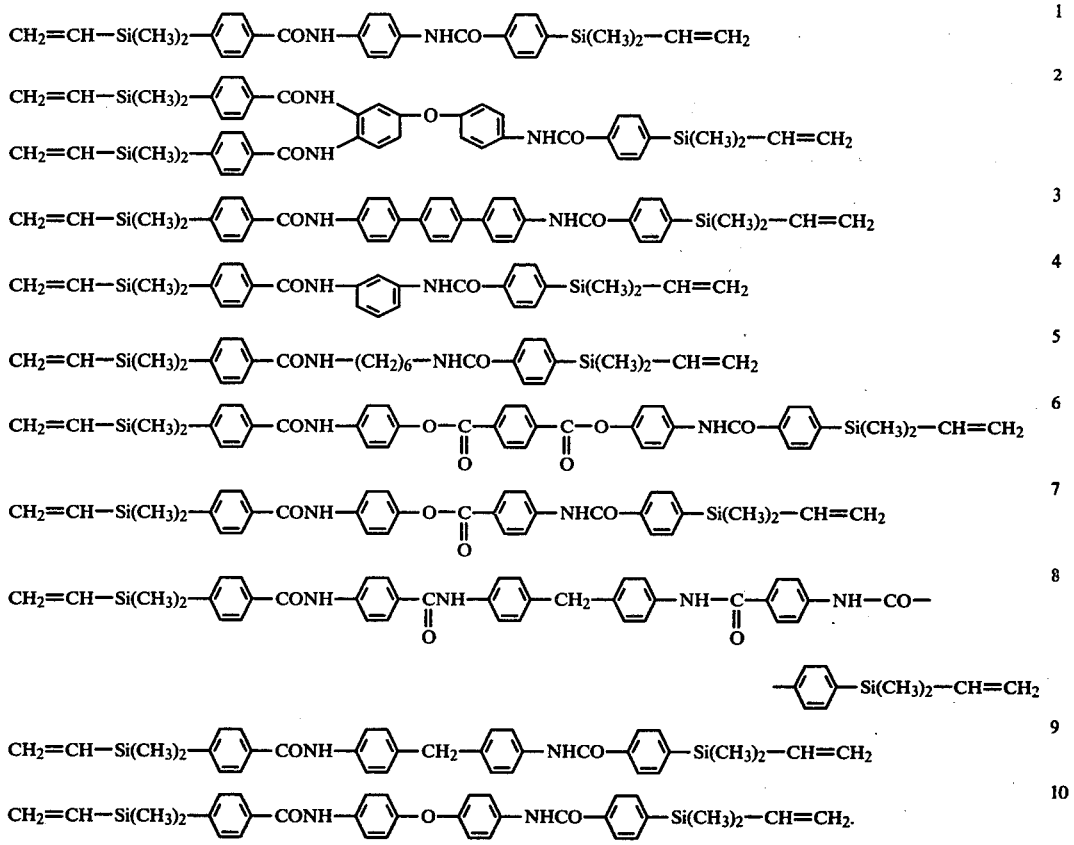

The compounds of the present invention can be prepared by reacting a silane of the formula:

$$R-Si(R_1)_2-G-Y_1 \quad (II)$$

with a compound of the formula:

$$(Y_2)_n Q \quad (III)$$

In these two formulas, the symbols R, $R_1$, G, Q and n have the meaning recited above. $Y_1$ and $Y_2$ represent groups which, as a result of the reaction, form the various groups represented by Y in formula I. Ordinarily, to obtain a group represented by Y, $Y_1$ is a radical selected from the group consisting of COOH, COOR$_2$, COCl, and COOM in which M represents sodium, potassium, or lithium and $R_2$ represents a linear or branched alkyl radical containing up to 4 carbon atoms. In such cases, $Y_2$ is either a NH$_2$ or OH radical, making the compounds of formula III polyols, polyphenols, polyamines, amino alcohols and aminophenols.

The quantities of the two reactants are initially chosen so that there is n moles of the silane of formula II per mole of the second reactant. The silane reactant is not required to be one particular product but may be a mixture of silanes corresponding to formula II. These silanes are prepared from other silanes having the formula:

$$R-Si(R_1)_2-G-Cl \quad (IV)$$

by application of conventional methods, such as, carbonation or esterification.

The silanes of formula IV are prepared by a reaction scheme utilizing an organomagnesium halide complex (Grignard reagent) according to the following process:

Step (a) Condensation of a dichlorinated Grignard reagent containing the radical G with a dichlorosilane:

$$Cl-G-MgCl+(R_1)_2SiCl_2 \rightarrow Cl-G-Si(R_1)_2Cl+MgCl_2 \quad (A)$$

Step (b) Condensation of product (A) with Grignard reagent, RMgCl:

$$(A)+RMgCl \rightarrow Cl-G-Si(R_1)_2-R+MgCl_2$$

Illustrative of the compounds represented by formula II which are useful as reactants in forming the compounds of the present invention are:
vinyldimethylsilyl-4 benzoic acid
chlorocarbonyl-1 vinyldimethylsilyl-4 benzene
divinylmethylsilyl-4 benzoic acid
methoxycarbonyl-1 vinyldimethylsilyl-4 benzene
ethoxycarbonyl-1 vinyldimethylsilyl- 4 benzene
ethoxycarbonyl-3 vinyldimethylsilyl-4 pyridine
vinyldimethylsilyl-4 methoxycarbonyl-4' diphenylmethane
vinyldimethylsilyl-4 methoxycarbonyl-4' diphenylether Exemplary of compounds represented by formula III which comprise the second reactant in preparing the compounds of the present invention are: (A) polyamines such as:
hexamethylenediamine
bis(amino-4 cyclohexyl)-2,2 propane
m-phenylenediamine
p-phenylenediamine triamino-1,2,4 benzene
m-xylylenediamine
p-xylylenediamine
bis(amino-4 phenyl) methane
diamino-4,4' phenyl oxide
diamino-4,4' benzophenone
diamino-4,4' benzoate of phenyl
N,N'bis(p-aminobenzoyl)diamino-4,4' diphenylmethane
bis p-(amino-4 phenoxy) benzene
diamino-2,6 pyridine (B) polyols or polyphenols such as:
ethylene glycol
propanediol-1,3
butanediol-1,4
pentanediol-1,5
hexanediol-1,6
heptanediol-1,7
bis($\delta$ hydroxybutyl)1,4 cyclohexane
bis($\beta$ hydroxyethyl)-1,4 benzene
hydroquinone
resorcinol
dihydroxy-1,5 naphthalene
dihydroxy-4,4' biphenyl
bis(hydroxy-4 phenyl) methane
bis(hydroxy-4 phenyl) sulfone (C) amino alcohol or aminophenols such as:
ethanolamine
amino-3 propanol-1
amino-4 butanol-1
amino-5 pentanol-1
amino-6 hexanol-1
amino-6 methyl-5 hexanol-1
amino-10 decanol-1
p-aminophenyl-4 cyclohexanol
p-hydroxymethylbenzylamine
hydroxymethyl-4 aminomethyl-4' biphenyl
(p-amino)phenethyl alcohol The reaction between the silane of formula II and the compound of formula III is brought about as a general rule at a temperature between about $-20°$ and $200°$ C., and preferably between about $-10°$ and $100°$ C. Usually, one of the reagents is introduced in the reactive environment containing the other reagent. Depending on the particular groups which are present, the reactive environment may additionally contain an acceptor of hydrochloric acid or a catalyzer of transesterification. As a general rule, the reaction occurs in the environment of a solvent, such as, N-methylpyrrolidone, dimethylacetamide, chloroform, methylene chloride, tetrahydrofurane, dioxane, ethyl ether, or isopropyl ether. After the reaction, the compounds of formula I can be isolated from the reactive environment by applying known methods, such as, precipitation, recrystallization.

The polyethylene silicon compounds which are the subject of the present invention can take part in many reactions because of the presence of unsaturated groups. In particular, they can allow reticulation of polyolefines or organosiloxanes in the presence of peroxides or radiation. They may also allow addition of mono- or bis-hydrogenated silanes or siloxanes with hydrolyzable or non-hydrolyzable function in order to prepare resins or elastomers, or they may lead to homopolymers by heating in the presence of a "radicalary initiator" or a source of radiation.

The following examples are provided to further illustrate the subject matter of the present invention, it being understood that in no way are they intended to limit the scope of the invention.

In the following examples, the silanes which were used as initial silanes (product of formula II) were dimethylvinylsilyl-4 benzoyl chloride (z). This product was prepared by action of thionyl chloride on the corresponding benzoic acid (y); the acid (y) was itself prepared from the corresponding chlorophenylsilane (x). These various products were prepared as follows:

PREPARATION OF P-CHLOROPHENYLSILANE DIMETHYL VINYL (X)

Forty cubic centimeters (0.33 mol) of dimethyldichlorosilane at 20° C. were placed in a three-neck balloon-flask swept by a flow of nitrogen. Eighty cubic centimeters of toluene were added while agitating the mixture. The temperature was changed to 5° C., then 0.33 mol of p-chlorophenylmagnesium chloride was added in 30 mn in the form of a solution in tetrahydrofurane (140 cubic centimeters). Twenty cubic centimeters of toluene were added and shaken for 2 hours 30 minutes. Them 0.36 mol of vinylmagnesium chloride was added in 20 mn in the form of a solution in tetrahydrofurane (120 cubic centimeters), with the temperature being maintained at 25° C. Then the temperature of the reactive environment was raised to 80° C. and maintained at that temperature for 2 hours. The reactive environment was cooled, the product was washed twice in 120 cubic centimeters of water acidified by 5 cubic centimeters of HCl. Then, after decantation, neutralization by means of bicarbonate of soda, drying, 42 grams of a product was collected containing (chromatography in gaseous phase) 80 percent by weight of p-chlorophenyldimethylvinylsilane (yield 51.3 percent as compared to dimethylchlorosilane.)

PREPARATION OF VINYLDIMETHYLSILYL-4 BENZOIC ACID (Y)

Twelve and one-half grams of magnesium in the form of shavings were packed in a three-neck balloon-flask under flow of nitrogen, then 10 cubic centimeters of "magnesian (a)" product (obtained from the previous operation) were poured in. The mixture was heated to 70° C., then 99 grams of dimethylvinylchlorophenylsilane as prepared above in the form of a solution in 150 cubic centimeters of THF were added. The pouring of chlorophenylsilane was completed in 2 hours. It was kept boiling (reflux of tetrahydrofurane THF) during 12 hours in order to complete the reaction, then the environment containing p-(dimethylvinylsilyl) phenylmagnesium chloride (a) was withdrawn. Two hundred cubic centimeters of THF were poured in a balloon-flask and cooled by a bath of ice/acetone and saturated with $CO_2$ by stirring. Then the magnesian product was poured in the balloon-flask while $CO_2$ was kept in excess and the temperature of the reactive environment was maintained around 10° C. This reactive environment was then poured in 2 liters of ice cold water acidified by 55 cubic centimeters of a solution of HCl 10 N. Two hundred-fifty cubic centimeters of toluene were added in order to stimulate the decantation of the resulting paste.

After washing, treatment in a basic environment, precipitation, 62 grams of a white product with a melting point of 82° C. were collected and identified as vinyldimethylsilyl-4 benzoic acid (yield of 61 percent as compared to dimethylvinylchlorophenylsilane).

PREPARATION OF DIMETHYLVINYLSILYL-4 BENZOYL CHLORIDE (Z)

The acid prepared in accordance with the preceding paragraph was used.

This acid (815 grams=3.75 mol) was placed in a balloon-flask and heated to 90° C. The product after shaking became a pasty liquid. In this environment, 595 grams (5 mols) of thionyl chloride were introduced in 1 hour 30 minutes. The reaction was endothermic. The reactive environment was maintained at 45° C. for 1 hour 20 minutes.

Dimethylvinylsilyl-4 benzoyl was obtained with a yield of 90.5 percent (as compared to dimethylvinylsilyl-4 benzoic acid). (Boiling point 98.5°–100° C. under pressure of 3 millimeters of mercury).

EXAMPLE 1

In a balloon-flask kept in an atmosphere of nitrogen and equipped with an agitation system, a condenser, a tap vial and a thermometer, 24.8 grams (0.125 m) of diamino-4,4' diphenylmethane and 150 millimeters of N-methylpyrolidone (NNP) were introduced. Fifty-seven and one-half grams (0.25 m) of dimethylvinylsilyl-4 benzoyl chloride was poured over a period of 1 hour in the solution which had been cooled to 5° C. The homogeneous reactive environment was kept for 3 hours at room temperature, then precipitated in 1 liter of ice cold water while being shaken energetically. After several washings, bis(dimethylvinylsilyl-4 benzamido-4' phenyl) methane was recrystallized in toluene. A white product was obtained. The yield was 57 percent as compared to dimethylvinyl-4 benzoyl chloride.

The infrared spectrum showed bands which were characteristic of the compound having the following formula:

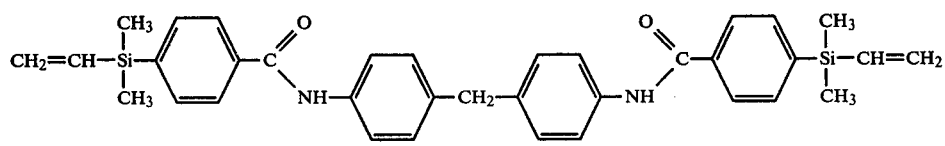

The instant melting point was 152° C.

The centesimal analysis with regard to C, H, and N gave the following results:
C%: 73.06–73.23
H%: 6.72–6.65
N%: 4.61–4.85

Chromatographic analysis of thin layer did not detect any impurity.

EXAMPLE 2

According to the operational conditions of Example 1, 45 grams (0.1 m) of bis(amino-4 benzamido-4' phenyl) methane and 250 millimeters of NMP were introduced. Forty-five grams (0.2 m) of dimethylvinylsilyl-4 benzoyl chloride were added over a period of 1 hour in the suspension cooled to 5° C.

The homogeneous reactive environment was kept for 2 hours at room temperature, then precipitated in 1.5 liters of ice cold water. The bis(dimethylvinylsilyl-4 dibenzamido-4',4" phenyl) methane was recrystallized in a mixture at the rate of 90/10 of DMF/water (volume/volume).

The infrared spectrum showed characteristic bands of the product of the following formula:

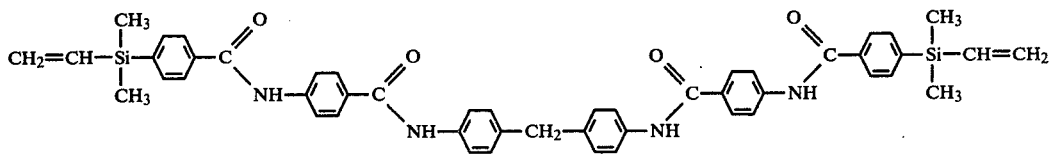

This white solid, which was obtained with a yield of 91 percent, had an instant melting point of 250° C.

Chromatographic analysis of a thin layer did not detect any impurities.

The centesimal analysis indicated the following:
C%: 70.27–70.32
H%: 5.86–6.04
N%: 7.50–7.33

EXAMPLE 3

In accordance with Example 1, 35 grams (0.1 m) of bis-(amino-4 phenyl) terephthalate and 300 millimeters of NMP were introduced. Forty-five grams (0.2 m) of dimethylvinylsilyl-4 benzoyl chloride were poured over a period of 1 hour in the solution which had been cooled to 5° C. The heterogeneous paste-like reactive environment was kept for 4 hours at room temperature, then precipitated in 1 liter of ice cold water. The bis(-dimethylvinylsilyl-4 benzamido-4' phenyl) terephthalate was recrystallized in dimethylformamide. The crystallized product was white. The yield was 81.5 percent. The instant melting point was 330° C.

The infrared spectrum corresponded to the product of the following formula:

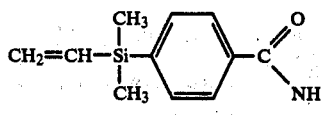
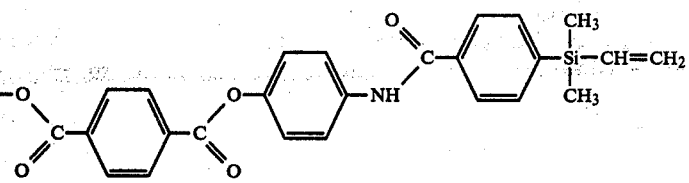

Chromatographic analysis of a thin layer did not detect any impurities.

The centesimal analysis indicated the following:
C%: 69.16–69.29
H%: 5.62–5.65
N%: 4.03–4.00

EXAMPLE 4

In accordance with Example 1, 24 grams (0.1 m) of amino-4 benzoate of 'amino-4' phenyl and 150 millimeters of NMP were introduced. Dimethylvinylsilyl-4 benzoyl chloride was added over a period of 1 hour in the solution which was cooled to 5° C. The homogeneous reactive environment was kept for 2 hours at room temperature, then precipitated in 1 liter of ice cold water. The dimethylvinylsilyl-4 benzamido-4' benzoate of (dimethylvinylsilyl-4" benzamido-4''') phenyl was recrystallized in alcohol.

A white amorphous product was collected with a yield of 73 percent. The instant melting point was 225° C.

The infrared spectrum corresponded to the product of the following formula:

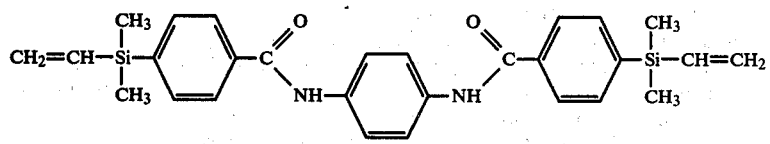

Chromatographic analysis of a thin layer detected the presence of a small quantity of aromatic impurity.

Centesimal analysis indicated the following:
C%: 69.10
H%: 5.98–6.10
N%: 4.24–4.50

EXAMPLE 5

In accordance with Example 1, 21.6 grams (0.2 m) of p-phenylene diamine and 200 millimeters of NMP were introduced. Ninety grams (0.4 m) of dimethylvinylsilyl-4 benzoyl chloride were added over a period of 1 hour in the suspension which was cooled to 5° C. The homogeneous reactive environment became heterogeneous when half of it was poured in, and paste-like at the end of the pouring. It was kept for 4 hours at room temperature, then precipitated in 1 liter of cold water. The p-phenylene bis(dimethylvinylsilyl-4 benzamide) was recrystallized in dioxane.

The product obtained with a yield of 82 percent was a white, crystalline compound. The instant melting point was 180° C.

The infrared spectrum showed the characteristic bands of the product of the following formula:

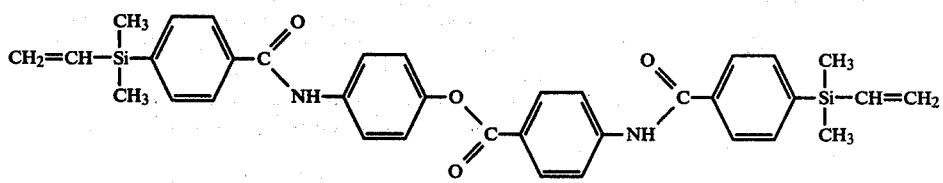

Chromatographic analysis of a thin layer detected the presence of a small quantity of aromatic impurity.

Centesimal analysis indicated the following:
C%: 69.33–69.30
H%: 6.46–6.52
N%: 5.74–5.63

EXAMPLE 6

In accordance with Example 1, 12.1 grams (0.1 m) of hexamethylene diamine and 200 millimeters of NMP were introduced. Forty-five grams (0.2 m) of dimethylvinylsilyl-4 benzoyl chloride were added over a period of 1 hour in the solution which was cooled to 5° C. The heterogeneous reactive environment was kept for 3 hours at room temperature, and then precipitated in 1 liter of ice cold water. The hexamethylene bis(dimethylvinylsilyl-4 benzamide) was recrystallized in cyclohexane.

The product obtained with a yield of 40 percent was white and crystalline in the form of flakes. The melting point was 128° C.

The infrared spectrum corresponded to the product of the following formula:

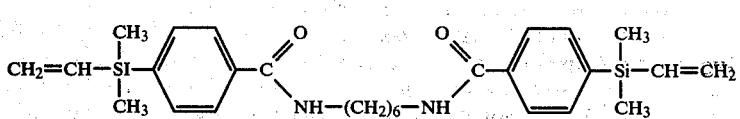

Chromatographic analysis of a thin layer did not detect any impurity.

Centesimal analysis indicated the following:
C%: 69.17–68.86
H%: 8.26–8.20
N%: 5.48–5.70 vinylsilyl-4 benzamide) was recrystallized in acetophenone.

A white product in the form of prismatic crystals was obtained with a yield of 89.5 percent. The melting point was 338° C.

The infrared spectrum corresponded to the product of the following formula:

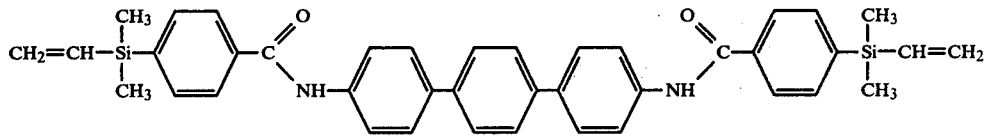

EXAMPLE 7

In accordance with Example 1, 10.9 grams (0.1 m) of m-phenylene diamine and 200 millimeters of NMP were introduced. Forty-five grams (0.2 m) of dimethylvinylsilyl-4 benzoyl chloride were added over a period of 1 hour in the solution which was cooled to 5° C. The homogeneous reactive environment was kept for 2 hours at room temperature, and then precipitated in 1 liter of ice cold water. The m-phenylene bis(dimethylvinylsilyl-4 benzamide) was recrystallized in a mixture of 75 25 alcohol/water (volume/volume).

A translucid, crystalline product in the form of flakes was collected with a yield of 77.5 percent.

The product had an instant melting point of 178° C.

The infrared spectrum showed the characteristic bands of the product of the following formula:

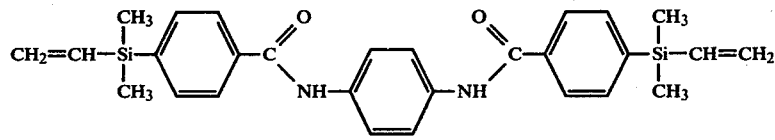

Chromatographic analysis of a thin layer detected the presence of an impurity which did not contain any amine.

Centesimal analysis indicated the following:
C%: 69.28–69.16
H%: 6.58–6.65
N%: 6.00–5.80

EXAMPLE 8

In accordance with Example 1, 25.08 grams (0.1 m) of p-terphenyl diamine and 200 millimeters of NMP were introduced. Forty-five grams (0.2 m) of dimethylvinylsilyl-4 benzoyl chloride were added over a period of 1 hour in the suspension which was cooled to 15° C. The heterogeneous reactive environment was heated for 2 hours to 75° C. The solution was precipitated in 1 liter of ice cold water. The p-terphenylene bis(dimethyl- Chromatographic analysis of a thin layer did not detect any impurity.

Centesimal analysis indicated the following:
C%: 76.41–76.33
H%: 6.41–6.51
N%: 4.27–4.50

EXAMPLE 9

In accordance with Example 1, 15.25 grams (2/30th m) of triamino-3,4,4' diphenyl ether and 150 millimeters of pyridine were introduced. Forty-five grams (0.2 m) of dimethylvinylsilyl-4 benzoyl chloride were added over a period of 1 hour in the solution which was cooled to 5° C. The homogeneous reactive environment was kept for 2 hours at room temperature, then precipitated in 1 liter of ice cold water. By dissolving the product in hot hexane and cooling it, tri-(dimethylvinysilyl-4 benzamido) 3',4',4" diphenyl ether was obtained.

The product obtained with a yield of 62 percent was beige in color and amorphous. The melting point was 162° C.

The infrared spectrum showed characteristic bands of the product of the following formula:

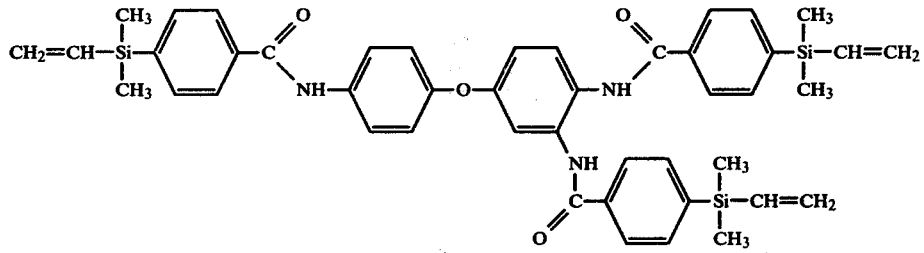

Chromatographic analysis of a thin layer detected the presence of a small quantity of impurities which did not contain any amines.

EXAMPLE 10

In accordance with Example 1, 40 grams (0.2 m) of diamino-4,4' diphenyl ether to dissolve in 100 cubic centimeters of NMP were introduced, then 93.48 grams of dimethylvinylsilyl-4 benzoyl chloride were added in the solution which was cooled to 0° C. over a period of 1 hour. The reactive environment was kept under agitation for 2 hours at room temperature, then precipitated in 1 liter of distilled water while the product was shaken energetically. The p-bis-(dimethylvinyl)silyl-N,N' benzamido-4,4' diphenyl ether was recrystallized in toluene.

A white product with a melting point of 185° C. was obtained with a yield of 68.2 percent.

The infrared spectrum corresponded to the product of the following formula:

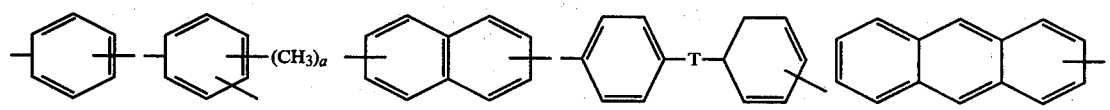

Centesimal analysis indicated the following:
C%: 71.00–71.23
H%: 6.36–6.36
N%: 4.77–4.88

While the invention has now been described in terms of certain preferred embodiments and exemplified with respect thereto, the skilled artisan will readily appreciate that various modifications, substitutions, changes and omissions, may be made without departing from the spirit thereof. Accordingly, it is intended that the scope of the invention be limited solely by that of the following claims.

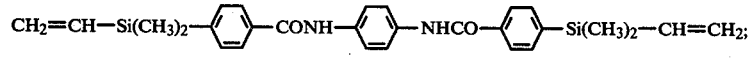

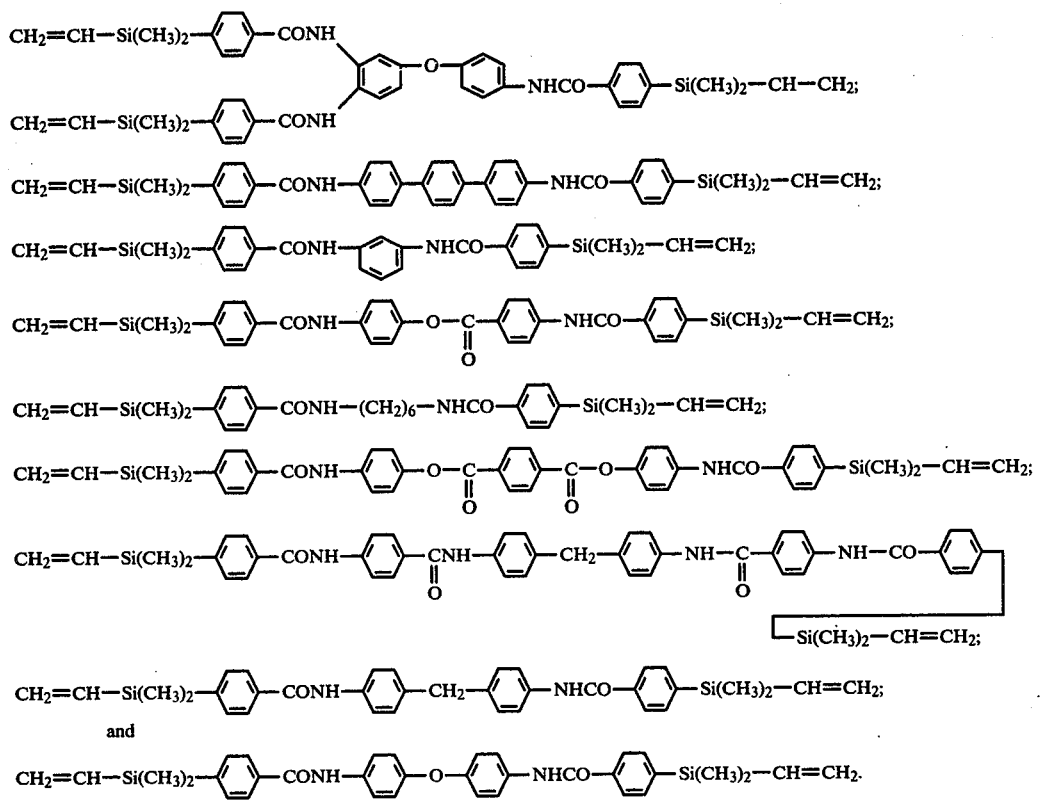

What is claimed is:

1. Organosilicon compounds having the general formula:

$$(R-Si(R_1)_2-G-Y)_nQ$$

wherein, R represents a monovalent aliphatic hydrocarbon or halocarbon radical containing up to 10 carbon atoms and including a carbon-carbon double bond; $R_1$ represents member selected from the group consisting of a monovalent hydrocarbon radical containing up to 10 carbon atoms, cycloalkyl radicals having 3 to 6 carbon atoms in the ring, aryl radicals, and the halo and cyano derivatives thereof; G represents a divalent carbocyclic aromatic radical; Q represents a radical of valence n selected from the group consisting of aliphatic and cycloaliphatic radicals containing up to 13 carbon atoms, and carbocyclic aromatic radicals; Y represents a member selected from the group consisting of CONH and COO; and, n is an integer equal to 2 or 3.

2. The organosilicon compounds defined by claim 1, wherein the radical represented by G is a polycyclic compound joined together by a single bond or a functional group selected from the group consisting of $CH_2$, $C(CH_3)_2$, O, $SO_2$, and CONH.

3. The organosilicon compounds defined by claim 1, wherein the radical represented by Q is an aromatic radical in which the benzene nuclei are joined by a single bond or a functional group selected from the group consisting of $CH_2$, $C(CH_3)_2$, O, COO and CONH.

4. The organosilicon compounds defined by claim 1, wherein, n is an integer equal to 2 or 3, R represents a radical selected from the group consisting of vinyl, allyl, dichloro-2,2-vinyl, trichloro-1,2,2-vinyl, butene-2-yl, propene-1-yl, butene-1-yl, and methyl-2-propene-1-yl; $R_1$ represents a radical selected from the group consisting of methyl, ethyl, trifluoro-4,4,4-butyl, phenyl, o-, m- or p-tolyl, xylyl, p- or m-chlorophenyl, dichloro-3,5-phenyl, trichlorophenyl, tetrachlorophenyl, β-cyanoethyl, and α-cyanopropyl; G represents a radical selected from the group consisting of:

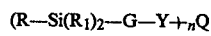

wherein a is an integer equal to 1 or 2 and T represents a single bond or O, $CH_2$, $C(CH_3)_2$ or $SO_2$; Q represents a divalent radical selected from the group consisting of pentamethylene, hexamethylene, cyclohexylene, the radicals represented by G and radicals containing 5 benzene nuclei joined together by single bonds or a functional group selected from the group consisting of O, $CH_2$, $C(CH_3)_2$, $SO_2$, COO and CONH.

5. A process for the preparation of the organosilicon compounds defined by claim 1, comprising reacting a silane of the formula:

(a) $R-Si(R_1)_2-G-Y_1$ with a compound of the formula (b) $(Y_2)_nQ$ wherein $Y_1$ and $Y_2$ represent groups which upon reaction form groups represented by Y and the quantities of the reactants (a) and (b) are chosen such that there exists n moles of compound (a) per mole of compound (b).

6. The process defined by claim 5, wherein $Y_1$ represents a radical selected from the group consisting of COOH, $COOR_2$, COCl and COOM in which M represents sodium, potassium or lithium and $R_2$ represents a linear or branched alkyl radical containing up to 4 carbon atoms and wherein $Y_2$ represents a radical selected from the group consisting of $NH_2$ and OH.

7. An organosilicon compound as defined by claim 1, selected from the group consisting of those of the structural formulae: